United States Patent [19]

Sarko y et al.

[11] Patent Number: 5,006,545
[45] Date of Patent: Apr. 9, 1991

[54] VETERINARY COMPOSITIONS AGAINST ENDOPARASITES CONTAINING CYPERMETHRIN AND ALBENDAZOLE

[75] Inventors: Peter Sarko y; László Pap; András Szegó, all of Budapest; Lajos Nagy, Szentendre; István Székely, Dunakeszi; Katalin Mármarosi, Biatorbagy; János Grosch, Budapest, all of Hungary

[73] Assignee: Chinoin Gyogyszer Es Vegyeszeti Termekek Gyara Rt., Budapest, Hungary

[21] Appl. No.: 391,780

[22] Filed: Aug. 9, 1989

[30] Foreign Application Priority Data

Aug. 9, 1988 [HU] Hungary ............................... 4128/88

[51] Int. Cl.$^5$ .................. A61K 31/34; A61K 31/415; A61K 31/425
[52] U.S. Cl. .................................... 514/395; 514/365; 514/461; 514/479; 514/521; 514/531
[58] Field of Search .................... 514/395, 5, 521, 531

[56] References Cited

U.S. PATENT DOCUMENTS 4,731,378  3/1988  Naik et al. ............................. 514/531
4,780,459 10/1988  Matthewson ........................... 514/521

OTHER PUBLICATIONS

Chemical Abstracts: vol. 99, No. 43566a (Evans et al.), (1983); vol. 111, No. 227197d (Wawrzyniak), (1988).
The Merck Index, 11th ed. (1989); Budavari (editor); pp. 200, 2774, 2871, 4069, 7129.

*Primary Examiner*—Mukund J. Shah
*Assistant Examiner*—Philip Datlow
*Attorney, Agent, or Firm*—Herbert Dubno; Jonathan Myers

[57] ABSTRACT

A veterinary composition is disclosed which is suitable against endoparasites and which contains as active ingredients:
(a) alpha-(cyano)-3-(2,2-dichlorovinyl)-2,2-dimethyl-cyclopropane-carboxylic acid-3-phenoxybenzyl ester or any isomeric mixture thereof; and
(b) 5(6)-propylthio-2-benzimidazolyl-methylcarbamate, wherein the weight ratio of the two respective compounds is 1:1 to 1.5:1, in combination with a carrier that is inert for veterinary purposes.

2 Claims, No Drawings

VETERINARY COMPOSITIONS AGAINST ENDOPARASITES CONTAINING CYPERMETHRIN AND ALBENDAZOLE

FIELD OF THE INVENTION

The invention relates to veterinary compositions usable against endoparasites containing as active ingredient at least one pyrethroid derivative of the formula I

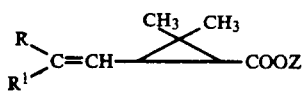

wherein

R and $R^1$ represent a $C_{1-4}$ alkyl group or halogen atom,

Z represents a group of the formula (a) or (b) or (c)

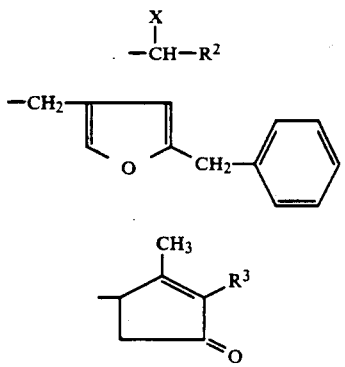

wherein

X stands for a hydrogen atom or cyano group, $R^2$ stands for tetrahydro-phthalimido or 3-phenoxyphenyl group and $R^3$ is allyl or 2,4-pentadienyl group or the isomeric mixture thereof in whatever ratio and optionally a benzimidazole derivative of the formula II

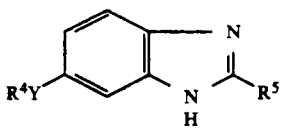

or an aniline derivative of the formula III

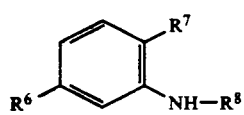

wherein

Y represents —O—, —S—, —NH—, —CO—, —SO—, —SO$_2$— or a valence bond, $R^4$ represents hydrogen atom, $C_{1-4}$ alkyl group or $C_{2-5}$ alkoxycarbonyl group or phenyl group, $R^5$ stands for a group of the formula —NH—COOR$^9$ or 4-thiazolyl group, $R^6$ stands for hydrogen atom, —S—$C_{1-4}$ alkyl or —S—phenyl group, $R^7$ stands for —NO$_2$ or —NHR$^{10}$ group, $R^8$ stands for a group of the formula —CSNHCOOR$^{11}$ or —C(NR$^{12}$)NHCOOR$^{13}$ or —COCH$_2$OR$^{14}$, $R^9$ stands for $C_{1-4}$ alkyl group, $R^{10}$ stands for a group of the formula —CSNHCOOR$^{11}$ or —C(NCOOR$^{15}$)NH—COOR$^{13}$, $R^{11}$ stands for $C_{1-4}$ alkyl group, $R^{12}$ stands for —(CH$_2$)$_2$—SO$_3$H group, $R^{13}$ stands for a $C_{1-4}$ alkyl group, $R^{14}$ stands for a $C_{1-4}$ alkyl group, $R^{15}$ stands for a $C_{1-4}$ alkyl group in an amount of 0.5–50 weight %, while optionally the ratio of the active ingredients of the formulae I and II or III is 1:7–1:1, in addition to the filling, diluting and other auxiliary agents generally used in veterinary therapeutics.

The compositions according to the invention contain as active ingredient of the formula I optionally one of a following compounds or the mixture thereof:

3-(2,2-dichlorovinyl)-2,2-dimethyl-cyclopropane carboxylic acid-3-phenoxybenzylester or 2,2-dimethyl-3-(2-methylpropenyl)-cyclopropane carboxylic acid-N-(hydroxymethyl)-1-cyclohexane-1,2-dicarboximide, or α-cyano-3-(2,2-dichlorovinyl)-2,2-dimethyl-cyclopropane-carboxylic acid-3-phenoxybenzylester or any isomeric mixture thereof;

as active ingredient of the formula II one of the following compounds:

5(6)-propylthio-2-benzimidazolyl-methylcarbamate,
5(6)-phenylthio-2-benzimidazolyl-methylcarbamate,
5(6)-sulphinyl-2-benzimidazolyl-methylcarbamate;

as active ingredient of the formula III one of the following compounds:

1,2-bis(3-ethoxycarbonyl-2-thioureido)benzene,
N-2-nitro-5-(propylthio)phenyl-N$^1$-(2-sulphoethyl)-amidinomethyl-carbamate.

The veterinary compositions according to the invention usable against endoparasites can be prepared in a manner that as active ingredient at least one pyrethroid derivative of the formula I—wherein R, $R^1$, $R^2$, $R^3$, X and Z are as defined above—or the isomeric mixture thereof in whatever ratio and optionally a benzimidazole derivative of the formula II or an aniline derivative of the formula III—where in the formulae Y, $R^4$, $R^5$, $R^6$, $R^7$, $R^8$, $R^9$, $R^{10}$, $R^{11}$, $R^{12}$, $R^{13}$, $R^{14}$ and $R^{15}$ have the same meaning as defined above—are mixed in an amount of 0.5 to 50 weight % with filling, diluting and other auxiliary agents generally used in the veterinary therapeutics, and transformed into veterinary compositions while optionally the ratio of the active ingredients of formulae I and II or III is 1:7–1:1.

The active ingredients are used in a form which is suitable for use in the veterinary therapeutics, such as: compositions usable for oral administration, such as pastes, emulsions, suspensions (drench), granules, powders, tablets, boluses, furthermore the so-called pour on (more liquid) and spot on (more concentrated) compositions which can be applied on to the skin surface. The pour on and spot on compositions, which are poured onto the intact skin surface, are prepared by dissolving the active ingredients in a suitable solvent or solvent mixture, by suspending or emulsifying.

The stability and usability of the individual oral compositions according to the invention is the most suitable if they are formulated in a form of inoculated lyotropic liquid crystals.

The inoculated lyotropic liquid crystalline veterinary compositions of the invention contain the above described active ingredients having a particle size under 100 μm in an amount of 0.5–50 weight %, 5 to 55 weight % of surfactants containing at least 8 carbon atoms, 0 to 67 weight % of water or the aqueous solution of non-surfactants, 0 to 40 weight % of water immiscible, water miscible or partly miscible solvents or the mixture thereof, or the water immiscible or partly miscible organic solvent solution of non-surfactants, 0 to 60 weight % of co-surfactants or the mixture thereof and optionally other additives, where the total amount of water, water miscible, immiscible or partly miscible solvents and the co-surfactants is 15 to 94.5 weight %.

The composition may be prepared in a manner that the solution or suspension containing related to the composition 5 to 55 weight % of surfactants having at least 8 carbon atoms, 0 to 67 weight % of water or the aqueous solution of non-surfactants, 0 to 40 weight % of water immiscible, miscible or partly miscible solvents, or the mixtures thereof, or the water immiscible or partly miscible organic solvent solution of non-surfactants, 0 to 60 weight % of co-surfactants or the mixture thereof and optionally other additives is inoculated with the active ingredients having a particle size under 100 μm described above and, if desired, further additives are given to the composition obtained.

As surfactants ionic (anionic and cationic) and/or non-ionic and/or amphoteric tensides, as anionic tensides the salts of carboxylic acids, such as fatty acid soaps, sulphates, such as alkylsulphates, optionally sodiumdodecylsulphate; salts of sulphonic acids, such as alkylbenzensulphonates; phosphates, such as alkylphosphates and the salts thereof; the esters of ethoxylated fatty alcohols formed with inorganic acids (preferably with sulphuric acid, phosphoric acid) and the salts thereof, as cationic tensides ammonium salts, such as cetyl-trimethylammoniumhalogenides, quaternary nitrogen containing compounds, such as N-alkyl-pyridinium salts; alkylamines or the salts of adducts formed of alkyl amines or alkylamides with ethyleneoxide, such as oxyethylated coconut fatty acid amide; as non-ionic tensides fatty acid esters of multivalent alcohols such as oxyethylated dianhydrosorbit-stearates-O-phosphoric acid trialkyl ester; ethylene oxide adducts such as fatty acid-polyethylene-glycolesters, fatty alcohol-ethyleneoxide-adducts, adducts of alkylphenols formed with ethyleneoxide, alkyl-phenolpoly(glycolether); adducts of alkylamines or alkylamides formed with ethyleneoxide, poly(propylenglycols)-ethyleneoxide-adducts, alkyl(polyethylenglycolether)-O-phosphorus acid triesters, as amphoteric tensides, preferably the inner salts of betaines or phophorus acid derivatives formed with choline can be used. As solvent water, aliphatic and/or aromatic solvents, such as mineral oils and ketones of low molecular mass, mono or multivalent alcohols and esters, plant and animal oils, $C_{1-6}$ saturated or unsaturated and above $C_6$ unsaturated carboxylic acids can be used.

As co-surfactants alcohols, ketones and esters, containing one or more polar group(s), such as fatty alcohols, e.g. i-octanol, dodecanol can be used.

In the inoculated liquid crystalline compositions of the invention preferably the mixture of ionic and non-ionic surface active agents is used as surface active agent in a total amount of 6–10 weight %.

The veterinary compositions of the invention can preferably be used against the insects and arthropodous endoparasites of different domestic and farm animals as well as for diagnostizing thereof.

BACKGROUND OF THE INVENTION

Helminthoses arising and often frequent among farm animals cause significant economic damages. According to estimations the gross profit in the cattle and sheep population is by 20–40 U.S. $ less per capita than would be expected on the basis of its potential. Among the economical losses the damage caused by parasites have an increasingly greater role in addition to the animal keeping, feeding and other veterinary problems. The endoparasites take the nutritive material necessary for their survival and multiplication from the host. The production of farm animals and sometimes even their life is exposed to danger.

The scope of the active ingredients used by the protection against nematodes is wide. These are for example phenotiazine, benzimidazoles, imidazoles, pyrimidines, pyridines, ivermectine, different organic phosphatesters, piperazine, isothiocyanate, certain substituted phenoles and salicylanilides.

The protection against internal parasites is extremely difficult because of the condition that in addition to nematodes, trematodes and cestodes livestock can be infected also by articulata. The articulata belonging to the species of Dipteras are e.g. the horse bot flies (*gastrophilidae*) causing the bottenness of horses, the gad-flies causing the gad-fly larva disease of cattle skin (*hypodermatidae*) and the gad-flies (*Oestridae*) causing the gad-fly larva disease of snout of the sheep.

The current anthelmintics—except ivermectine—are, however, ineffective against Dipteras. Therefore per os administered phosphatetester type insecticides are used against these flies in themselves or combined with an anthelmintic.

Such composition is e.g. Rintal Plus sold by the firm Bayer, which is a mixture of a probendazole—namely phebantel—and trichlorfon in a ratio of 1:5 with an active ingredient content of 42.7 weight %. An analogous composition is Combotel. Another composition containing mebendazole and trichlorfon in a ratio of 8.8:40 is Telmin B. The composition Equizole-B of Merck contains also thiabendazole and trichlorfon in a ratio of 44:40. Mixtures of oxybendazole:trichlorfon are used in similar manner in ratios of 1:3.5 (Vet. Med., 1985, Apr. p. 68) and 1:3 (Vet. Rec., 1986, Sept., p. 294). Another phosphatetester, dichlorvos (Astrobot) is also widely used. Such compositions are Equigard and Equigel (Squibb).

The organic phosphatester insecticides being effective for colinergic synapses are, however, not selective and their oral administration is therefore very hazardous. Their therapeutic index is so low that even double the overdosage thereof has toxic effect. As is known horses are sensitive to treatments with trichlorfon (Vet. Med., 1985, Apr., p. 68) which are accompanied by diarrhoea, frequent defecation and urination. The treatment of animals of poor health and bad condition is therefore contraindicated.

Among insecticides pyrethroids have developed fastest during the last decades. Already more than 20 active ingredients are today at the disposal of agricultural, veterinary and sanitarian workers. But compositions containing a pyrethroid as active ingredient usable against the endoparasite articulata of farm animals are unknown. The possible reason for this is that pyrethroids, as insecticides effective against adult flies and having knock down activity are known and no practical importance has been attached to their activity against larvas of flies and worms.

One of the most important characteristics of the pharmaceutical compositions is the quotient of toxic and therapeutic dosage, the so-called therapeutic index characterizing the security of use. The higher is this value, the smaller is the risk in use, the selective is the active ingredient.

OBJECT OF THE INVENTION

Knowing the unfavorable selectivity of the current active ingredients against endoparasite articulata the object was to develop a composition of greater effectivity and higher therapeutic index.

SPECIFIC DESCRIPTION

For this purpose the activity of several pyrethroid insecticides has been tested per se or in combination with different benzimidazole type anthelmintics on flies (*Musca domestica*). Considering the complete larval development it was found that several per se ineffective benzimidazole derivatives significantly increased the effectivity of pyrethroids. This synergistic interaction was shown not only in the decrease of the therapeutical concentrations but also on the activity of the sublethal doses to the development. The body mass of the larvas is decreased and from the little aurelias evolved during the long development often deformed imagos, unsuitable for further multiplication were hatched out. Above all the synergistic interaction has made possible the decrease of the therapeutic dose of the orally administered insecticide.

On the basis of the results of the laboratory examinations and toxicity data the therapeutic dose usable for treating bot infection of horses was determined in field trials. Surprisingly it was found that some pyrethroids and pyrethroid+benzimidazole mixtures were so effective against the larvas (bots) of the parasite Gastrophylus species that—considering also their warm blooded toxicity—their selectivity index was by two orders higher than that of the compositions having a similar field of use.

The therapeutic indexes of current anthelmintics and transmix each having insecticidal activity and suitable for per os administration are shown in Table 1.

TABLE 1

| Anthelmintic/ insecticide | Toxicity+ acute per os LD$_{50}$ (mg/kg) | Therapeutic dose++ (mg/kg) | Therapeutic index (selectivity) |
|---|---|---|---|
| Dichlorvos | 56 | 5 | 11 |
| Trichlorfon | 450 | 30 | 15 |
| Ivermectine | 10 | 0.2 | 50 |
| Transmix | 5000 | 2 | 2500 |

+measured on rats
++against horse bots

EXAMPLE 1

For examining the interaction between benzimidazoles and pyrethroids the larvas of domestic flies in L$_3$ status (*Musca domestica* WHO/SRS) were used as model organism.

A nutriment suitable for breeding fly larvas was prepared from yeast, milk, bran and water and the nutriment was portioned into plastic glasses. Acetonic strain solution was prepared from the active ingredients and after dilution the amounts necessary for achieving the desired active ingredient concentrations were added to the nutriment in the plastic glasses.

The examinations were carried out with total active ingredient concentrations of 1, 5, 10, 50, 100 and 200 ppm in 6 parallel tests per each concentration. Into the plastic glasses containing the treated culture medium 20—20 domestic fly-larvas of L$_3$ status were placed after mass measurement. The glasses were covered by gauze and after 12 days the hatched imagos were counted. In the control containing only solvent the hatching ratio was 91%, the average weight of the hatched flies was 18.2 mg.

The results are shown in Table 2.

TABLE 2

| Active ingredient | Concentration (ppm) | | | | | |
|---|---|---|---|---|---|---|
| | 1 | 5 | 10 | 50 | 100 | 200 |
| | number of hatched imagos (from 120 L$_3$) | | | | | |
| Chinmix | 90 | 62 | 47 | 27 | 4 | 0 |
| Transmix | 108 | 112 | 89 | 64 | 39 | 18 |
| Albendazole | 111 | 113 | 107 | 112 | 107 | 109 |
| Chinmix + Albendazole+ | 91 | 44 | 25 | 15 | 0 | 0 |
| Transmix + Albendazole+ | 110 | 95 | 63 | 34 | 21 | 3 |
| Transmix + Albendazole++ | 106 | 98 | 69 | 44 | 26 | 0 |

+pyrethroid:benzimidazole ratio = 1:1
++pyrethroid:benzimidazole ratio = 1.5:1.

EXAMPLE 2

Fly larvas of L$_3$ status were grown in identical manner as in an Example 1, on a nutriment having a total active ingredient concentration of 5 and 10 ppm.

The average body mass of the larvas before hatching and of the imagos after treatment is shown in Table 3.

TABLE 3

| Active ingredients | Concentration (ppm) | |
|---|---|---|
| | 5 | 10 |
| | average body mass (hatching %) | |
| Chinmix | 10.3 (53) | 7.8 (41) |
| Transmix | 12.9 (98) | 9.6 (84) |
| Abendazole | 18.3 (100) | 17.8 (100) |
| Chinmix + Albendazole+ | 7.3 (43) | 4.2 (25) |
| Transmix + Albendazole++ | 95 (88) | 5.6 (61) |

+pyrethroid:albendazole ratio = 1.1
++pyrethroid:albendazole ratio = 1.5:1

The data of the Table show that the combinations give an outstanding result not only concerning the mortality values.

The treatments with sublethal dose significantly hinder the puparial development which is shown by the decreased body mass of the hatching imagos. The decreased vitality and issue producing of the flies having smaller body mass further increases the effectivity of treatments.

EXAMPLE 3

A trial was carried out in June, 1988 on 24 horses ageing 2-5 years (13 geldings, 8 mares, 3 stud horses; considering their types: 8 gidrans and 16 Hungarian halfbreds). 18 horses divided into two groups (in group A 6, in group B 12) were treated per os with the composition of Example 4 in a dose of 20 g/600 kg (=10 mg/kg albendazole+1.5 mg/kg transmix). To the control animals (6 horses) a paste was given which did not contain active ingredient.

After the addition of the composition of Example 4 and the control paste of no active ingredient content, all the removed Gasterophylus intestinal larvas were determined in the spontaneously defecated faeces samples for 72 hours. The results are shown in Table 4.

TABLE 4

| Animal population | Staff number | Total number of the eases larvas (pieces) |
|---|---|---|
| A | 6 | $302L_3 + 24L_4$ |
| B | 12 | $48L_3$ |
| Control | 6 | — |
| A + B | 18 | $350L_3 + 24 L_4$ |

EXAMPLE 4

110 g of saccharose was dissolved in 256.5 g of ion exchanged water at 35° C. The solution was cooled back to 20° C. and 50 g of propylenglycol, 75 g of Tween 60 (product of ICI) were added to the solution. To the solution mixed with a stirred (Vitra Turrex) of great shearing force 333 g os Albendazole, then 50 g of Transmix were added. When preparing the suspension the mixture was cooled in such a manner that the temperature does not exceed 40° C.

To the solution 12 g of fatty alcohol polyglycolether dissolved in 108 g of paraffin oil, then the solution of 4.5 g of 96% alcohol and 1 g of Nipagin is added. The suspension is homogenized for 30 seconds by using a great shearing force.

The composition shows up in a microscopic picture characteristic to the of lyotropic liquid crystals.

The agents used in the specification correspond to the following active ingredients:

ivermectine: dihydro-avermectine $B_1$ febantel: (2-(2-methoxyacetamido)-4-(phenylthio)-phenyl)-imidocarbonyl-dimethyl-dicarbamate trichlorofon: 2,2,2-trichloro-1-hydroxyethyl-phosphonic acid dimethylester mebendazole: 5(6)-benzoyl-benzimidazole-N-methylcarbamate thiabendazole: 2-(4¹-thiazolyl)-benzimidazole oxybendazole: 5(6)-propoxybenzimidazole-N-methylcarbamate dichlorvos: 2,2-dichlorovinyl-phosphonic acid dimethylester albendazole: 5(6)-propylthio-benzimidazole-N-methylcarbamate transmix: α-cyano-3-(2,2-dichlorovinyl)-2,2-dimethyl-cyclopropan-carboxylic acid-3-phenoxybenzylester 1RtransS and 1StransR enantiomer pair chinmix:
α-cyano-3-(2,2-dichlorovinyl)-2,2-dimethyl-cyclopropan-carboxylic acid-3-phenoxybenzylester
a mixture of the enantiomer pairs of 1RcisS++1-ScisR and 1RtransS+1StransR in a ratio of 55:45–25:75.

What is claimed is:

1. A veterinary composition suitable against endoparasites containing as active ingredients:
   (a) alpha-(cyano)-3-(2,2-dichlorovinyl)-2,2-dimethyl-cyclopropane-carboxylic acid-3-phenoxybenzyl ester or any isomeric mixture thereof; and
   (b) 5(6)-propylthio-2-benzimidazolyl-methylcarbamate, wherein the weight ratio of the two respective compounds is 1:1 to 1.5:1, in combination with a carrier that is inert for veterinary purposes.

2. A method of treating an infection caused by an endoparasite in a domesticated animal subject which comprises the step of orally administering to said domesticated animal subject, a therapeutically effective amount of the veterinary composition defined in claim 1.

* * * * *

UNITED STATES PATENT AND TRADEMARK OFFICE
CERTIFICATE OF CORRECTION

PATENT NO. : 5,006,545

DATED : 9 April 1991

INVENTOR(S) : Peter SARKOZY et al

It is certified that error appears in the above-identified patent and that said Letters Patent is hereby corrected as shown below:

TITLE PAGE: below line [19], for the inventors' name read

-- SARKOZY et al --;

Line [75] for the first inventor's name read -- Peter Sarkozy --.

Signed and Sealed this

Eighteenth Day of August, 1992

*Attest:*

DOUGLAS B. COMER

*Attesting Officer*  *Acting Commissioner of Patents and Trademarks*